(12) United States Patent
Chen et al.

(10) Patent No.: US 11,299,548 B2
(45) Date of Patent: Apr. 12, 2022

(54) GENE COMBINATION CAPABLE OF HIGH-EFFICIENCY EXPRESSION OF RECOMBINANT HUMAN NERVE GROWTH FACTOR

(71) Applicant: Xintrum Pharmaceuticals, Ltd., Jiangsu (CN)

(72) Inventors: Hai Chen, Nanjing (CN); Hongliang Sun, Nanjing (CN); Yi Zhang, Nanjing (CN); Yuesheng Wang, Nanjing (CN)

(73) Assignee: XINTRUM PHARMACEUTICALS, LTD., Nanjing (CN)

( * ) Notice: Subject to any disclaimer, the term of this patent is extended or adjusted under 35 U.S.C. 154(b) by 34 days.

(21) Appl. No.: 16/954,354

(22) PCT Filed: Nov. 8, 2018

(86) PCT No.: PCT/CN2018/114594
§ 371 (c)(1),
(2) Date: Jun. 16, 2020

(87) PCT Pub. No.: WO2019/184372
PCT Pub. Date: Oct. 3, 2019

(65) Prior Publication Data
US 2020/0385477 A1    Dec. 10, 2020

(30) Foreign Application Priority Data

Mar. 26, 2018    (CN) .......................... 201810252273.3

(51) Int. Cl.
*C12N 15/18*    (2006.01)
*C07K 16/28*    (2006.01)
*A61K 38/18*    (2006.01)

(52) U.S. Cl.
CPC ........ *C07K 16/2875* (2013.01); *A61K 38/185* (2013.01)

(58) Field of Classification Search
None
See application file for complete search history.

*Primary Examiner* — Joanne Hama
*Assistant Examiner* — Jon M Lockard
(74) *Attorney, Agent, or Firm* — Yong Chen; Lin Sun-Hoffman; Liu Chen & Hoffman LLP

(57) ABSTRACT

A gene combination capable of high-efficiency expression of rhNGF is provided to optimize gene expression regulation components of a recombinant human nerve growth factor. The gene combination enhances expression of rhNGF. As shown by experiments, the gene combination is capable of high-efficiency expression of a recombinant human nerve growth factor (rhNGF) with natural activity in a eukaryotic expression system.

6 Claims, 3 Drawing Sheets
Specification includes a Sequence Listing.

SEQUENCE LISTING

<160> NUMBER OF SEQ ID NOS: 10

<210> SEQ ID NO 1
<211> LENGTH: 150
<212> TYPE: DNA
<213> ORGANISM: Artificial Sequence
<220> FEATURE:
<223> OTHER INFORMATION: Synthetic

<400> SEQUENCE: 1

```
ctcgactgat cacaggtaag tatcaaggtt acaagacagg tttaaggaga ccaatagaaa      60
ctgggcttgt cgagacagag aagactcttg cgtttctgat aggcacctat tggtcttact     120
gacatccact ttgcctttct ctccacaggt                                      150
```

<210> SEQ ID NO 2
<211> LENGTH: 296
<212> TYPE: DNA
<213> ORGANISM: Artificial Sequence
<220> FEATURE:
<223> OTHER INFORMATION: Synthetic

<400> SEQUENCE: 2

```
gaattaattc gctgtctgcg agggccagct gttggggtga gtactccctc tcaaaagcgg      60
gcatgacttc tgcgctaaga ttgtcagttt ccaaaaacga ggaggatttg atattcacct     120
ggcccgcggt gatgcctttg agggtggccg cgtccatctg gtcagaaaag acaatctttt     180
tgttgtcaag cttgaggtgt ggcaggcttg agatctggcc atacacttga gtgacaatga     240
catccacttt gcctttctct ccacaggtgt ccactcccag gtccaactgc aggtcg         296
```

<210> SEQ ID NO 3
<211> LENGTH: 90
<212> TYPE: DNA
<213> ORGANISM: Artificial Sequence
<220> FEATURE:
<223> OTHER INFORMATION: Synthetic

<400> SEQUENCE: 3

```
atggactcta aaggctcctc tcagaagggt agtaggctgc tgctgctgct ggtggtgtca      60
aatctgctgc tgtgccaggg ggtcgtcagc                                       90
```

<210> SEQ ID NO 4
<211> LENGTH: 30
<212> TYPE: PRT
<213> ORGANISM: Bos taurus

<400> SEQUENCE: 4

```
Met Asp Ser Lys Gly Ser Ser Gln Lys Gly Ser Arg Leu Leu Leu Leu
1               5                   10                  15
Leu Val Val Ser Asn Leu Leu Leu Cys Gln Gly Val Val Ser
            20                  25                  30
```

<210> SEQ ID NO 5
<211> LENGTH: 51
<212> TYPE: DNA
<213> ORGANISM: Artificial Sequence
<220> FEATURE:
<223> OTHER INFORMATION: Synthetic

<400> SEQUENCE: 5

```
atgggtgtca aggtcctgtt cgcactgatt tgtatcgccg tcgcagaagc c                51
```

<210> SEQ ID NO 6
<211> LENGTH: 17
<212> TYPE: PRT
<213> ORGANISM: Gaussia

<400> SEQUENCE: 6

Met Gly Val Lys Val Leu Phe Ala Leu Ile Cys Ile Ala Val Ala Glu
1               5                   10                  15

Ala

<210> SEQ ID NO 7
<211> LENGTH: 663
<212> TYPE: DNA
<213> ORGANISM: Artificial Sequence
<220> FEATURE:
<223> OTHER INFORMATION: Synthetic

<400> SEQUENCE: 7
gagcctcata gtgaatcaaa cgtgcctgct ggccacacca tcccacaggc acattggaca       60
aagctgcagc acagcctgga cacagctctg aggcgggcac gctctgcccc agccgctgca      120
atcgccgctc gcgtcgccgg acagactcga atattaccg tggaccccag gctgttcaag       180
aaaagacgcc tgcgatcacc tcgtgtcctg ttttccactc agcccctcg agaggcagcc       240 gatacccagg acctggattt cgaagtgggc ggagctgcac ccttcaacag acccaccgg       300 agtaagagat ccagctctca ccccatcttc catcggggg agttctccgt gtgcgattcc       360
gtgagcgtct gggtgggtga caaaaccaca gctacagata tcaagggcaa agaggtcatg      420
gtgctgggag aagtcaatat taacaattcc gtgttcaagc agtacttctt tgaaactaaa      480
tgccgtgacc caaaccccgt cgattccggg tgtagaggta ttgactctaa gcattggaat      540
agttattgta ctaccacaca cacatttgtg aaggccctga ctatggatgg caaacaggcc      600
gcttggagat tcattcgtat tgacactgct tgcgtctgcg tgctgagtcg taaggctgtg      660
cgg                                                                    663

<210> SEQ ID NO 8
<211> LENGTH: 221
<212> TYPE: PRT
<213> ORGANISM: Homo sapiens

<400> SEQUENCE: 8

Glu Pro His Ser Glu Ser Asn Val Pro Ala Gly His Thr Ile Pro Gln
1               5                   10                  15

Ala His Trp Thr Lys Leu Gln His Ser Leu Asp Thr Ala Leu Arg Arg
                20                  25                  30

Ala Arg Ser Ala Pro Ala Ala Ala Ile Ala Ala Arg Val Ala Gly Gln
            35                  40                  45

Thr Arg Asn Ile Thr Val Asp Pro Arg Leu Phe Lys Lys Arg Arg Leu
        50                  55                  60

Arg Ser Pro Arg Val Leu Phe Ser Thr Gln Pro Pro Arg Glu Ala Ala
65                  70                  75                  80

Asp Thr Gln Asp Leu Asp Phe Glu Val Gly Gly Ala Ala Pro Phe Asn
                85                  90                  95

Arg Thr His Arg Ser Lys Arg Ser Ser Ser His Pro Ile Phe His Arg
            100                 105                 110

Gly Glu Phe Ser Val Cys Asp Ser Val Ser Val Trp Val Gly Asp Lys
        115                 120                 125

```
Thr Thr Ala Thr Asp Ile Lys Gly Lys Glu Val Met Val Leu Gly Glu
    130                 135                 140

Val Asn Ile Asn Asn Ser Val Phe Lys Gln Tyr Phe Glu Thr Lys
145                 150                 155                 160

Cys Arg Asp Pro Asn Pro Val Asp Ser Gly Cys Arg Gly Ile Asp Ser
                165                 170                 175

Lys His Trp Asn Ser Tyr Cys Thr Thr His Thr Phe Val Lys Ala
            180                 185                 190

Leu Thr Met Asp Gly Lys Gln Ala Ala Trp Arg Phe Ile Arg Ile Asp
        195                 200                 205

Thr Ala Cys Val Cys Val Leu Ser Arg Lys Ala Val Arg
    210                 215                 220

<210> SEQ ID NO 9
<211> LENGTH: 54
<212> TYPE: DNA
<213> ORGANISM: Artificial Sequence
<220> FEATURE:
<223> OTHER INFORMATION: Synthetic

<400> SEQUENCE: 9
atgtcaatgc tgttttacac tctgattacc gcttttctga tcggaatcca ggcc      54

<210> SEQ ID NO 10
<211> LENGTH: 18
<212> TYPE: PRT
<213> ORGANISM: Homo sapiens

<400> SEQUENCE: 10

Met Ser Met Leu Phe Tyr Thr Leu Ile Thr Ala Phe Leu Ile Gly Ile
1               5                   10                  15

Gln Ala
```

GENE COMBINATION CAPABLE OF HIGH-EFFICIENCY EXPRESSION OF RECOMBINANT HUMAN NERVE GROWTH FACTOR

BACKGROUND OF THE INVENTION

1. Technical Field

The present disclosure relates to biotechnology and, more particularly, to a gene combination capable of high-efficiency expression of a recombinant human nerve growth factor (rhNGF) with natural activity in a eukaryotic expression system.

2. Description of Related Art

Nerve growth factors (NGF) have dual biological functions, i.e., provide nutrients to neurons and promote axonal growth, and thus NGFs are important to regulation of development, differentiation, growth and regeneration of central and peripheral neurons and expression of functional characteristics thereof.

NGFs synthesized in vivo come in the pro form (proNGF), including "gene B", leader peptide and mature NGFs. The "gene B" facilitates secretion of protein. Two conservative regions of the leader peptide are required for proNGF expression, intracellular cleavage which results in formation of protein with biological function, secretion of mature NGFs, and facilitating the correct folding of protein. Each proNGF includes potential N-glycosylation sites. The glycosylation of leader peptide in the proNGF is conducive to its exit from endoplasmic reticulum. After being hydrolyzed at specific sites in the presence of furin or prohormone convertase, the proNGF turns into mature NGF with biological activity. The mature NGF has 118 amino acids and a double-chain dimer structure. Each chain has a total of six cysteine residues and three corresponding pairs of intrachain disulfide bonds ($Cys^{58}$-$Cys^{108}$, $Cys^{68}$-$Cys^{110}$, $Cys^{15}$-$Cys^{80}$). The correct formation of disulfide bonds is a prerequisite for the activity of the NGFs.

China is the first and only country which permits commercial use of mNGF (mouse nerve growth factor) for injection. There are 10% differences in amino acid sequence between mNGF (mouse nerve growth factor) and hNGF (human nerve growth factor). Hence, as a extractive heterologous protein, mNGF poses potential safety issues and mouse-related viral infection risk when in long use.

In the 1990s, pharmaceutical industries and research institutes operating outside China started studying recombinant human nerve growth factors, but no rhNGF products have ever been rendered commercially available. This is the case because of unsatisfactory NGF expression, unsatisfactory expression product biological activity, and homology issues between hNGF and mNGF.

For instance, the rhNGF eye drop solution developed by Italy-based Dompé was approved by the European Medicines Agency in Jul. 6, 2017 for the treatment of moderate to severe neurotrophic keratitis. The rhNGF is expressed in the form of proNGF in *E. coli* expression system. The system lacks any effective post-translation modification function to the detriment of the correct folding of mature NGF protein. The expression products are inclusion bodies. The subsequent process requires in vitro renaturation. It is only when leader peptide is digested by protease that the target protein is obtained. The aforesaid unfavorable features lead to disadvantages, such as intricate production process, low production yield, and high production cost.

High-efficiency expression of rhNGF in a eukaryotic expression system is currently in need of a resolution. It is because high-efficiency expression of a vector is the primary factor in attaining high production yield of rhNGF. The expression of rhNGF is enhanced by using appropriate expression regulation sequence and reasonable structural arrangement in the course of construction of an expression vector.

BRIEF SUMMARY OF THE INVENTION

It is an objective of the present disclosure to optimize gene expression regulation components of a recombinant human nerve growth factor and provide a gene combination capable of high-efficiency expression of rhNGF.

The inventor of the present disclosure discovers that appropriate regulation components can be selectively connected to human nerve growth factor pro gene (hereinafter abbreviated as proNGF gene) so as to enhance expression of rhNGF in a eukaryotic expression system.

The present disclosure provides a gene combination capable of high-efficiency expression of rhNGF, wherein the combination is "gene B-gene A".

The gene A has nucleotide sequence shown in SEQ ID NO: 7 and known as proNGF gene, comprising leader peptide gene, mature hNGF, and coding for the amino acids of the sequence shown in SEQ ID NO: 8.

The gene B has nucleotide sequence shown in SEQ ID NO: 3 (Pre for short) or shown in SEQ ID NO: 5 (Luc for short), coding for the amino acids of the sequence shown in SEQ ID NO: 4 or SEQ ID NO: 6.

The present disclosure provides another gene combination capable of high-efficiency expression of rhNGF, further comprising a component of gene C, with the connection sequence being "gene C-gene B-gene A".

The gene C has nucleotide sequence shown in SEQ ID NO: 1 (glo for short) or shown in SEQ ID NO: 2 (aden for short).

As shown by experiments, the gene combination of the present disclosure enhances rhNGF secretion efficacy and thus enhances expression of rhNGF.

The gene combination is applied to an expression vector.

The expression vector is a eukaryotic expression vector and is introduced into host cells by instantaneous transfection or stable transfection.

The host cells are mammalian cells. The mammalian cells are Chinese hamster ovary (CHO) cells, human embryonic kidney 293 cells, COS cells or Hela cells.

The present disclosure entails performing research as follows:

1. Search protein sequence database UniProtKB for the amino acid sequence of hNGF and obtain the proNGF sequence which has the ID of P01138, as shown in SEQ ID NO: 8. Genscript Biotech Corporation optimally reversely-translates proNGF amino acid sequence into DNA sequence shown in SEQ ID NO: 7 in accordance with features of CHO cell expression and synthesizes it.

2. Add "gene B" Pre, Luc to the terminal 5' of proNGF, as shown in SEQ ID NO: 3, SEQ ID NO: 5, to obtain different "gene B"-proNGF gene combination, insert it into a eukaryotic expression vector, introduce it into CHO cells by instantaneous transfection, culture it, subject it to centrifugal separation, take supernatant, assay rhNGF content in the supernatant by ELISA, identify coded amino acid sequence as shown in SEQ ID NO: 10 using the control, i.e., natural "gene B" of proNGF whose gene sequence is shown in SEQ ID NO: 9 (Nat for short), and compare rhNGF expression levels under the guidance of different "gene B".

3. Apply "gene C" glo (shown in SEQ ID NO: 1), aden (shown in SEQ ID NO: 2) each to the expression vector mentioned in the preceding paragraph 2 with restriction endonuclease to obtain the eukaryotic expression vector which contains "gene C"-"gene B"-proNGF gene combination and evaluate the effect of "gene C" on rhNGF instantaneous expression by the method mentioned in the preceding paragraph 2 using the vector mentioned in the preceding paragraph 2 as the control.

4. Transfect the expression vector into the CHO cells mentioned in the preceding paragraph 3 and add thereto puromycin and methotrexate (MTX) to perform pressurized screening twice, so as to attain a cell pool.

5. Select the cell pool which manifests high specific yield and satisfactory cellular growth and perform monocloning and screening by limiting dilution analysis so as to attain an engineering cell strain capable of high-efficiency expression of rhNGF.

6. Assess the growth curves and cell survival rates of the engineering cell strains cultured in a biological reactor and the trend of variations in rhNGF expression level.

7. Assess biological activity of rhNGF by TF-1 cell/MTS colorimetry.

As shown by experiments, the "gene B-proNGF" gene combination of the present disclosure demonstrates a markedly higher rhNGF instantaneous expression level than NGF natural gene combination in a eukaryotic expression system (see embodiment 1).

Adding "gene C" to terminal 5' of the "gene B-proNGF gene" combination further markedly increases the rhNGF instantaneous expression level (see embodiment 1). The engineering cell strain constructed in accordance with the "gene C-gene B-proNGF" gene combination is cultured in a biological reactor, resulting in a 78 mg/L expression level of rhNGF in the supernatant (see embodiments 2, 3) and biological activity equal to that of international standard products, and stronger than that of mNGF for injection (see embodiment 4).

DETAILED DESCRIPTION OF THE INVENTION

Figure 1:
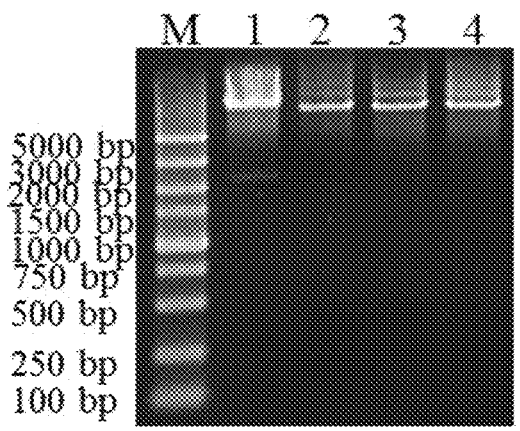
FIG. 1: SfiI digestion test of eukaryotic expression vector p-Pre/Nat/Luc-pro-rhNGF (SfiI) −1 which includes "gene B"-proNGF gene combination, wherein:
M: DL5000 DNA Marker;
1: p-Pre-pro-rhNGF-8,SfiI digestion;
2: p-Pre-pro-rhNGF(SfiI)-1,SfiI digestion;
3: p-Nat-pro-rhNGF(SfiI)-1,SfiI digestion;
4: p-Luc-pro-rhNGF(SfiI)-1,SfiI digestion.

The embodiments below are illustrative of the methods and devices of the present disclosure rather than restrictive of the scope of the present disclosure.

Embodiment 1 is about Determination of Gene Combination of rhNGF

1. Acquisition of ProNGF Gene

Search protein sequence database UniProtKB for the amino acid sequence of rhNGF and obtain the sequence which has the ID of P01138. The amino acid sequence of proNGF consists of leader peptide with 103 amino acids and mature hNGF with 120 amino acids, wherein two amino acids (RA) at terminal C do not have any effect on biological activity of NGF, nor are the two amino acids found in natural NGF protein. Hence, according to the present disclosure, proNGF amino acid sequence consists of leader peptide with 103 amino acids and hNGF with 118 amino acids, as shown in SEQ ID NO: 8. Genscript Biotech Corporation optimally reversely-translates proNGF amino acid sequence into DNA sequence shown in SEQ ID NO: 7 in accordance with features of CHO cell expression and synthesizes it.

2. Selection of Expression System

A mammalian cell expression system undergoes expression of rhNGF, including CHO cells and a eukaryotic expression vector. The CHO cells function as host cells. The eukaryotic expression vector comprises two insertion points and can simultaneously express two genes. A second expression unit can be removed as needed, and a single gene expression vector is constructed. The vector contains a dihydrofolate reductase selection mark and a puromycin-resistant gene which are for use in the simultaneous pressurized screening of MTX and puromycin and the enhancing of screening quality.

3. Screening of "Gene B" Component

"Gene B" Pre and "gene B" Luc guide secretion expression of rhNGF and are compared with natural "gene B" Nat of hNGF.

3.1 Acquisition of "Gene B"-proNGF Gene Combination

The "gene B" Pre gene sequence (shown in SEQ ID NO: 3) and proNGF gene sequence are jointly synthesized by Genscript Biotech Corporation to obtain a sequence (hereinafter abbreviated as Pre-pro-rhNGF). Terminals 5', 3' are provided with AvrII and BstZ17I digestion sites, respectively, and constructed on plasmid pUC57 to form plasmid pUC57-Pre-pro-rhNGF. Gene Pre-pro-rhNGF is obtained by performing double digestion on plasmid pUC57-Pre-pro-rhNGF with restriction endonuclease AvrII, BstZ17I. A Pre-pro-rhNGF gene segment with a size of about 770 bp is obtained by double digestion and purified by a plastic recycling reagent box so as to be reserved for later use. "Gene B" Luc, Nat, whose gene sequences are shown in SEQ ID NO: 5, SEQ ID NO: 9, are added to terminal 5' of proNGF gene through a guide and by PCR method, using pUC57-Pre-pro-rhNGF as a template, to obtain two gene segments (Luc-pro-rhNGF and Nat-pro-rhNGF for short) with a size of about 740 bp each. The PCR product is purified with a conventional DNA product purification reagent box, and its concentration is measured with a UV scanning spectrophotometer. After the purification, genes Luc-pro-rhNGF, Nat-pro-rhNGF undergo double digestion and purification in the presence of restriction endonuclease AvrII, BstZ17I so as to be reserved for later use.

3.2 Construction of Eukaryotic Expression Vector which Contains "Gene B"-proNGF Gene Combination The proNGF gene including different "gene B" is applied to the downstream part of EF2/CMV hybridization promoter of a eukaryotic expression vector, performing double digestion on the expression vector in the presence of restriction endonuclease AvrII, BstZ17I, and purifying the digestion product with a DNA purification reagent box.

Genes Pre-pro-rhNGF, Luc-pro-rhNGF, Nat-pro-rhNGF which result from double digestion performed in the presence of AvrII, BstZ17I are connected to the expression vector which results from double digestion by T4 DNA ligase, and a connector is chemically converted to Top 10 competent cells. Positive clones are obtained from a single bacterial colony which results from conversion and growth by bacterial PCR screening. If a target gene is successfully connected to the expression vector, the PCR product will be about 1000 bp in size, and the PCR product of an empty vector will be about 260 bp in size.

The positive clones p-Pre-pro-rhNGF-8, p-Nat-pro-rhNGF-1, p-Luc-pro-rhNGF-5 which result from PCR screening are chosen to undergo sequence detection. Sequence comparison and analysis shows that "gene B"-proNGF gene combination sequence of the three vectors is consistent with theoretic sequence.

To express rhNGF, it is necessary to remove the second expression unit (CMV/EF1 expression frame) from the eukaryotic expression vector but keep the first expression unit therein, thereby turning the eukaryotic expression vector into a vector which expresses only one unit. Removal of CMV/EF1 expression frame entails using restriction endonuclease SfiI to digest vectors p-Pre-pro-rhNGF-8, p-Nat-pro-rhNGF-1, p-Luc-pro-rhNGF-5 whose sequences are correctly detected. After the digestion product has been purified with a DNA product purification reagent box, vectors of SfiI digestion are mutually connected by T4 DNA ligase. A connector is chemically converted to Top 10 competent cells. A single bacterial colony thus grown is screened for positive clones by bacterial PCR. If the vector of CMV/EF1 expression frame is successfully removed, the PCR product will be free of any band, otherwise the PCR product is a band with a size of 535 bp.

Figure 2:
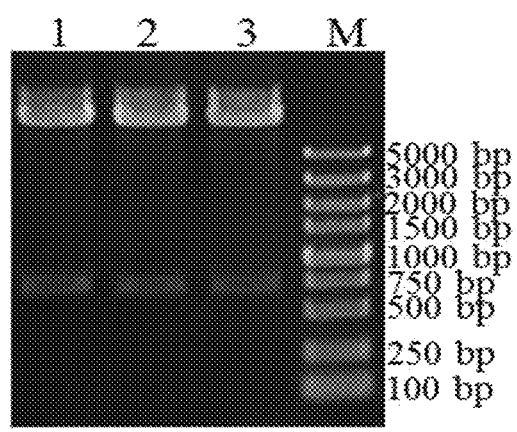
FIG. 2: AvrII, BstZ17I double digestion test of eukaryotic expression vector p-Pre/Nat/Luc-pro-rhNGF (SfiI) −1 which includes "gene B"-proNGF gene combination, wherein:
M: DL5000 DNA Marker;
1: p-Pre-pro-rhNGF(SfiI)-1,AvrII, BstZ17I double digestion;
2: p-Nat-pro-rhNGF(SfiI)-1,AvrII, BstZ17I double digestion;
3: p-Luc-pro-rhNGF(SfiI)-1,AvrII, BstZ17I double digestion.

According to the screening result of bacterial PCR, a single bacterial colony of a band-free PCR product is selected to extract plasmid p-Pre-pro-rhNGF (SfiI) −1, p-Nat-pro-rhNGF (SfiI) −1, p-Luc-pro-rhNGF (SfiI) −1, which are cut by SfiI single digestion, AvrII, BstZ17I double digestion test, and band-free SfiI single digestion of positive clones, respectively, as shown in FIG. 1, whereas bands with a size of about 740 bp are cut by AvrII, BstZ17I double digestion, as shown in FIG. 2.

The plasmid p-Pre/Nat/Luc-pro-rhNGF (SfiI) −1, which is digested and assayed correctly, undergoes sequence detection. Sequence comparison and analysis shows that the sequence of the "gene B"-proNGF gene combination inserted into the three expression vectors is consistent with the design sequence.

3.3 Effect of "Gene B"-proNGF Gene Combination on rhNGF Expression

The efficacy of rhNGF expression by various "gene B"-proNGF gene combinations is tested by instantaneous transfection.

(1) CHO Cell Culture Conditions

Culture medium FortiCHO is supplemented by 8 mM glutamine to become a complete culture medium. Culture conditions: orbital shaker (orbital diameter of 2.5 cm), rotation speed of 130 rpm, carbon dioxide concentration of 8%, and temperature of 37° C. As soon as their cell density increases to $1.5-2.5 \times 10^6$/mL, CHO cells must be subcultured. Their cell density is $3-5 \times 10^5$/mL after the subculture.

(2) Cell Transfection Method

One day before transfection, the cells are subcultured such that their cell density is $5-6 \times 10^5$/mL. Prior to transfection, the cell density is changed to $1 \times 10^6$/mL by the complete culture medium. An appropriate transfection volume is selected according to an experimental objective. Linearized expression vectors p-Pre/Nat/Luc-pro-rhNGF (SfiI) −1 and optiPRO SFM are added to a 1.5 mL micro centrifuge tube by the proportion of 1.67 g per $10^6$ to-be-subcultured cells, respectively, to attain a final volume of 50 L per $10^6$ to-be-subcultured cells and then gently blended. FreeStyle Max transfection reagent and optiPRO SFM are added to another 1.5 mL micro centrifuge tube by the proportion of 1.67 L per $10^6$ cells and 48.33 L per $10^6$ cells, respectively, and then gently blended. The diluted Max solution and DNA solution are immediately mixed and kept at room temperature for 20 minutes or less, preferably 10 minutes. The DNA: MAX mixture solution is added to a cell suspension drop by drop and then immediately placed in a shaker culture.

(3) Assessment of rhNGF Expression Level

Figure 3:
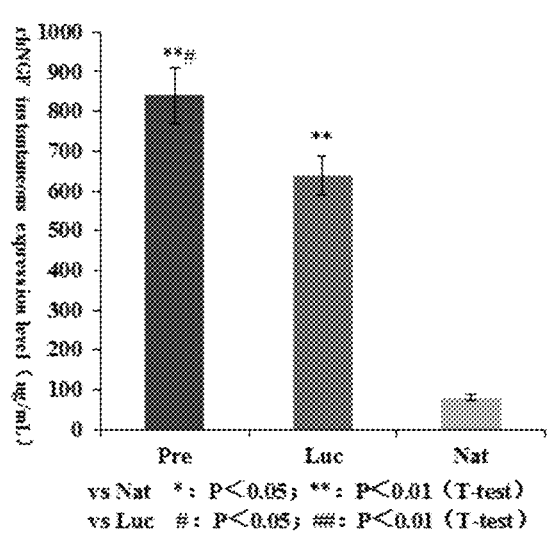
FIG. 3: Its two diagrams show experimental results of the effect of two instances of "gene B"-proNGF gene combination on rhNGF instantaneous expression, respectively.
Figure 3:
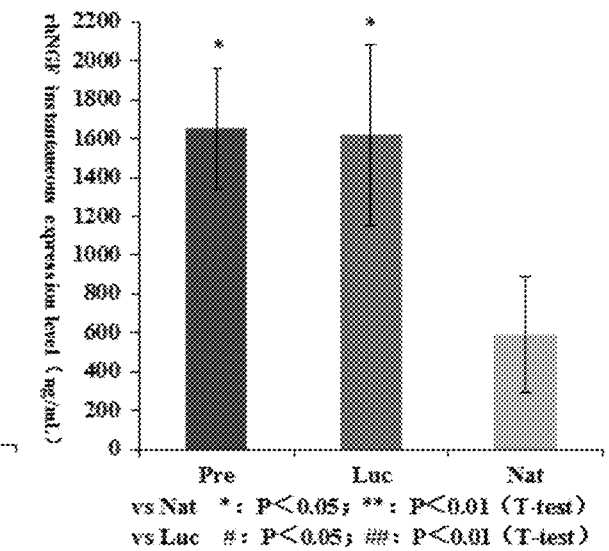

Upon completion of instantaneous transfection, the cell culture is sampled for 48 hours, and then expression levels of rhNGF are measured by ELISA under the guidance of the different "gene B", before a self-contained experiment is carried out twice, as shown in FIG. 3. The result shows that "gene B" Pre and Luc-proNGF gene combination demonstrate markedly higher rhNGF expression levels than NGF natural gene combination Nat-proNGF. Therefore, Pre, Luc "gene B" and proNGF gene combination are better options.

4. Selection of "Gene C" Component

Adding "gene C" to terminal 5' of a target gene enhances stability of mRNA and thereby augments expression of target albumen. The "gene C" glo and aden, whose sequences are shown in SEQ ID NO: 1 and SEQ ID NO: 2, are combined with "gene B" and proNGF gene, and then the effect of the combination on rhNGF expression is observed.

4.1 Acquisition of "gene C"

DNA sequences of "gene C" glo and aden are synthesized and constructed on the same plasmid pUC57 by Genscript Biotech Corporation to attain respective sizes of 150 bp and 296 bp. The two terminals of each sequence contain AvrII digestion sites, and the corresponding plasmid is known as pUC57-glo-aden. The glo and aden are obtained by performing single digestion on plasmid pUC57-glo-aden in the presence of restriction endonuclease AvrII and then purified with a plastic recycling reagent box so as to be reserved for later use.

4.2 Construction of Eukaryotic Expression Vector which Contains "Gene C"-"Gene B"-proNGF Gene Combination The "gene C" is added to the vector p-Pre-pro-rhNGF (SfiI) −1 which manifests higher levels of instantaneous expression of rhNGF as mentioned in the preceding paragraph 3. It undergoes digestion in the presence of restriction endonuclease AvrII, and the digestion product is purified with a conventional DNA product purification reagent box. The "gene C" segments glo, aden, which result from AvrII digestion, are connected to vector p-Pre-pro-rhNGF (SfiI) by T4 DNA ligase. A connector is chemically converted to Top 10 competent cells. Positive clones are obtained from a single bacterial colony which results from conversion and growth by bacterial PCR screening and named p-glo-Pre-pro-rhNGF(SfiI) and p-aden-Pre-pro-rhNGF(SfiI). The recombinant genes in the two vectors undergo sequence detection. Sequence comparison and analysis shows that the sequences of "gene C" glo, aden are consistent with the design sequence and thereby obtains a eukaryotic expression vector which contains "gene C"-"gene B"-proNGF gene combination.

4.3 Effect of "Gene C"-"Gene B"-proNGF Gene Combination on rhNGF Expression

Similarly, the efficacy of rhNGF expression by "gene C"-"gene B"-proNGF gene combination is tested by instantaneous transfection. The "gene C" is studied under the same CHO cell culture conditions and by the same cell transfection method as described in paragraph 3.3.

Figure 4:
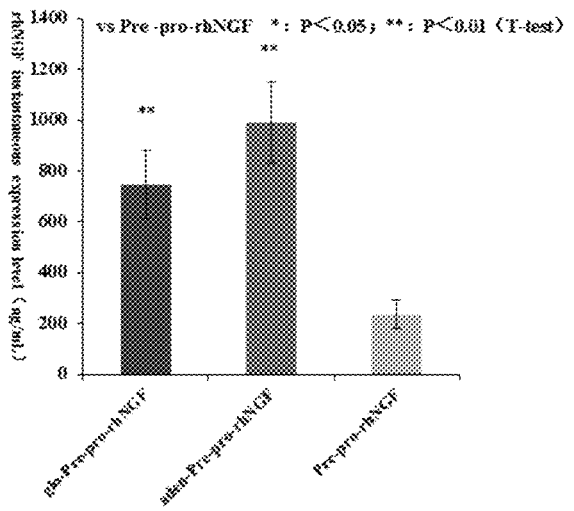
FIG. 4: Its two diagrams show experimental results of the effect of two instances of "gene C"-"gene B"-proNGF gene combination on rhNGF instantaneous expression, respectively.
Figure 4:
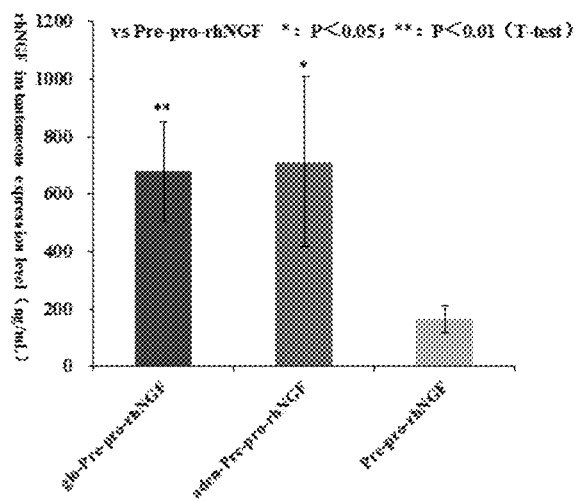
Figure 5:
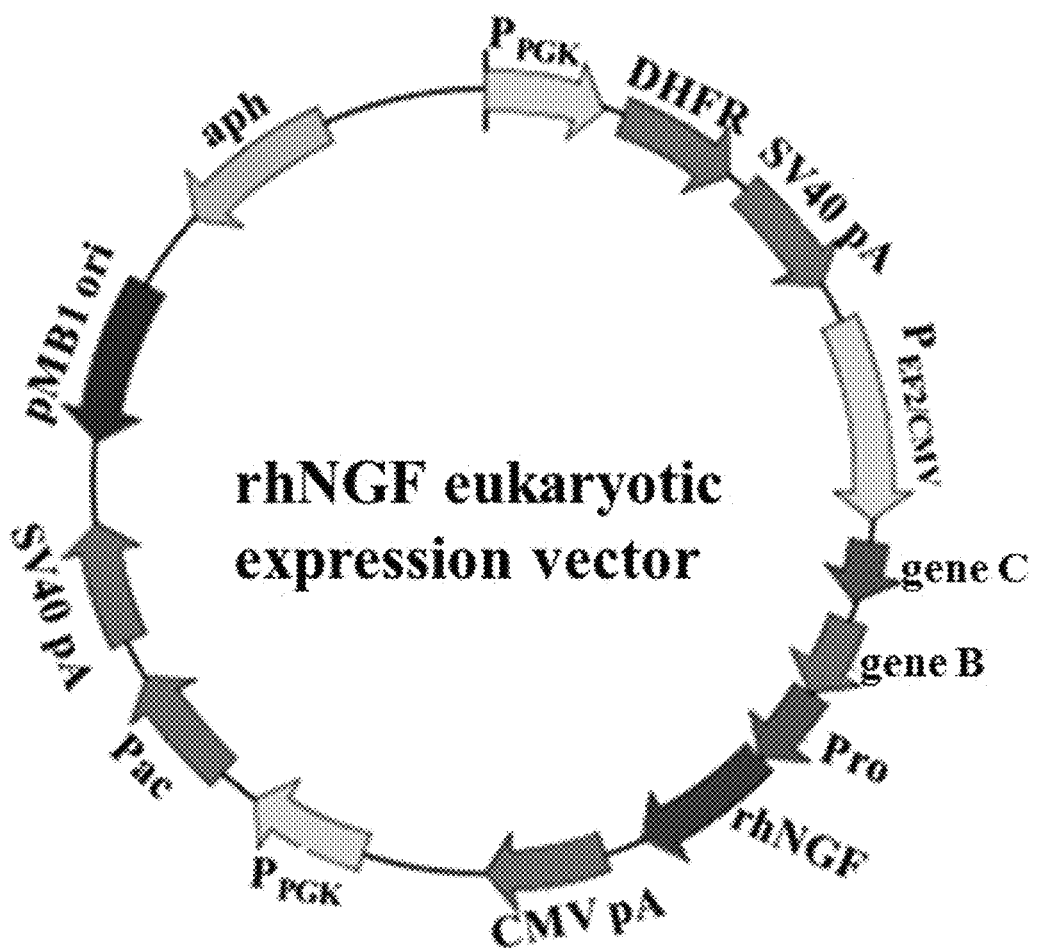
FIG. 5: It is a schematic view of rhNGF eukaryotic expression vector which includes "gene C"-"gene B"-proNGF gene combination, wherein:
"gene C", "gene B", pro sequence (Pro) and mature NGF sequence (rhNGF) together constitute a complete recombinant gene combination.

Linearized p-glo-Pre-pro-rhNGF(SfiI) and p-aden-Pre-pro-rhNGF(SfiI) expression vectors instantaneously transfect CHO cells and are cultured for 48 hours before being sampled. Expression efficacy is evaluated by testing the rhNGF content in the supernatant by ELISA. A self-contained experiment is carried out twice, as shown in FIG. 4. The result shows that adding "gene C" to terminal 5' of "gene B"-proNGF gene combination further markedly increases rhNGF expression levels, without any marked difference between two "gene C". Therefore, it is confirmed that "gene C"-"gene B"-proNGF gene combination is a preferred option for expressing rhNGF. The gene component combination inserted into the corresponding eukaryotic expression vector includes, consecutively, "gene C", "gene B", and proNGF gene, as shown in FIG. 5.

Embodiment 2: Construction of Engineering Cell Strain

1. Refer to Paragraph 3.3 for CHO Cell Culture Conditions and Cell Transfection Method.

2. Stable Screening

After transfection has lasted 48 hours, the cells are divided into two portions. 10 μg/mL puromycin and 100 nM MTX are added to one portion of the cells. 20 g/mL puromycin and 200 nM MTX are added to the other portion of the cells. After cell survival rate has been restored to over 85%, each portion of the cells is divided into two parts. 30 μg/mL puromycin/500 nM MTX is added to one part of the cells. 50 μg/mL puromycin/1000 nM MTX is added to the other part of the cells. After that, screening continues. The screening will end if the cell survival rate is greater than 90%. Two instances of screening bring about six cell pools. After specific yield has been analyzed, the cell pool which manifests high specific yield and satisfactory cellular growth is selected for use in monocloning.

3. Limiting Dilution Analysis: Monocloning and Clone Screening

The clone culture medium is FortiCHO supplemented by 6 mM glutamine. The cells to be cloned are diluted to 2-5 cells per mL. The cell suspension is introduced into a 96-well plate with an 8-channel pipette, with each well containing 200 μL of the cell suspension. The cells are cultured in a carbon dioxide incubator at 37° C. in the presence of 5% carbon dioxide. The cells are thus cultured for 11-14 days according to the cloning speed. After that, 20 μL of the cultured cells is taken out of the wells where monoclone is generated and then analyzed by ELISA for the concentration of rhNGF. The clones with high expression levels are selected and moved from the 96-well plate to a 48-well plate. 200 μL of fresh culture medium is added to the 48-well plate. The introduction of MTX and puromycin screening chemicals continue until the attainment of concentration for pre-monocloning cell pool screening. When fully grown, the clones are subcultured to a 12-well plate. The cells in the 12-well plate substantially reach subculture density, and then the cells are moved to the centrifuge tube for centrifugal separation and thereby supernatant removal. After the cells have been rinsed with PBS, the rinsed cells are contained in 1 mL of fresh culture medium by heavy suspension. Then, the cell-containing fresh culture medium is introduced into a 6-well plate, and 30 μL of cell suspension is taken out for analysis of cell density. Afterward, the 6-well plate is placed in the incubator culture for 2-4 hours. Next, 100 μL of the culture solution undergoes centrifugal separation to gather the supernatant. Then, 1 mL of fresh culture medium and screening chemicals are introduced into each of the wells in the 6-well plate to continue with the cultivation. The culture supernatant is analyzed by ELISA for rhNGF concentration. The specific yield of the cells is calculated by a related formula, with the specific yield being equal to rhNGF concentration/cell density/incubation duration. The clones undergo the second-instance screening in accordance with the specific yield.

Figure 6:
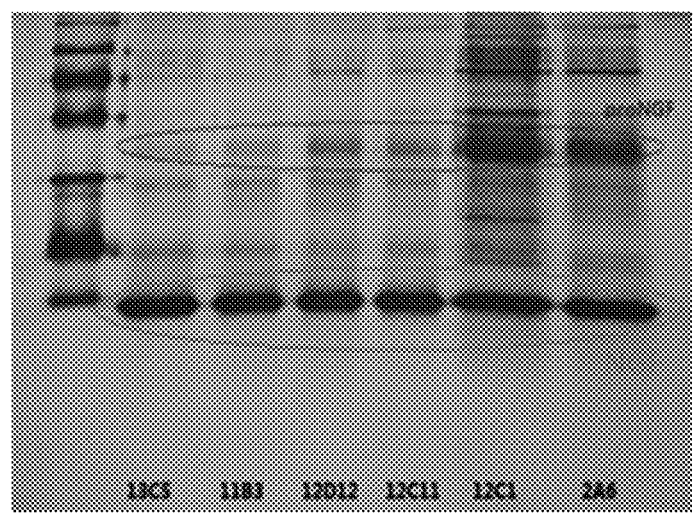
FIG. 6: Six strains of cell are cultured by batches with supernatant Capto-S purification before they are analyzed by SDS-PAGE.

The cells which have been obtained by screening undergo a subculture stability test. Six strains of cells which perform well in the stability test are selected to undergo batch cultivation. The rhNGF in the batch culture supernatant is preliminarily purified by Capto S column chromatography and then subjected to a SDS-PAGE test; the result is shown in FIG. 6, showing low proNGF albumen content in the rhNGF of 13C5 cell expression in the batch culture. Since proNGF albumen is product-related impurity, its low content is desirable; consequently, 13C5 cells are selected to be the engineering cell strain.

Figure 7:
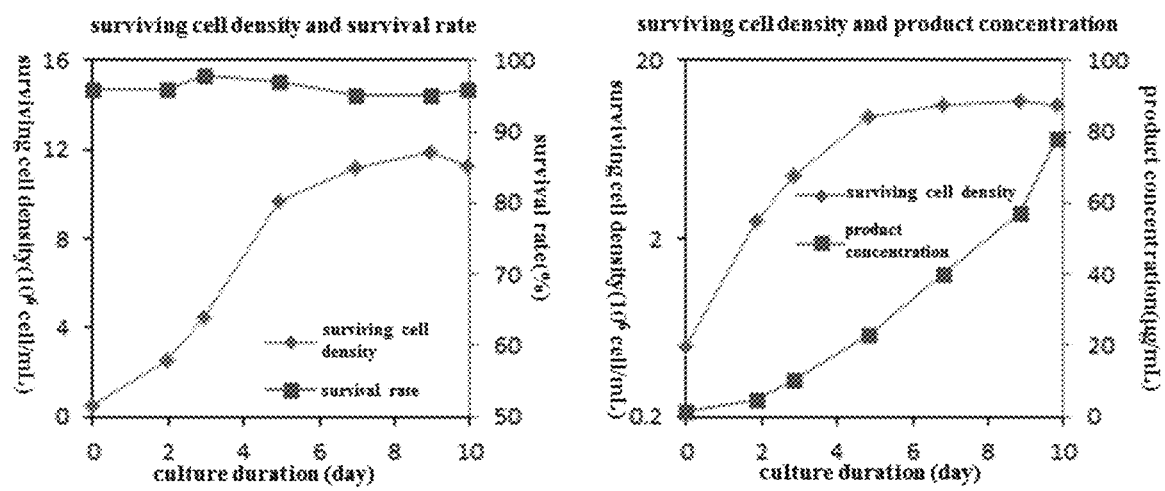
FIG. 7: Its two diagrams show growth curves and cell survival rates of the engineering cell strains cultured in a biological reactor and the trend of variations in rhNGF expression level.

Embodiment 3: Assess the Growth Curves and Cell Survival Rates of the Engineering Cell Strains Cultured in a Biological Reactor and the Trend of Variations in rhNGF Expression Level Fed-batch (supplement) culture serves as the production culture mode for the engineering cell strain. The culture scale increases from the 30 mL of a shake flask to 2.5 L and then further to the 28 L scale of a mechanical blending biological reactor capable of in-situ sterilization. The blending blades are single oblique blades capable of operating and blending at a rotation speed of 125 rpm, achieving ventilation with large bubbles. Dissolved Oxygen control precedes cascade control when exercising control over air flow rate. After a predetermined maximum gas flow rate has been reached, commencement of introduction of oxygen is accompanied by reduction in air flow rate, thereby keeping the total flow rate unchanged. During the initial stage of cultivation, pH is kept at 7.2 by controlling $CO_2$ flow rate. The course of cellular growth sees a decrease of pH and then an increase of pH to 7.2. Afterward, the pH 7.2 is maintained by diluted hydrochloric acid until the end of cultivation. In the course of cell cultivation, samples are collected regularly to monitor cell density, survival rate and concentration of rhNGF. The summarized result is shown in FIG. 7.

The result is as follows: on day 5, the cells switch from the exponential growth phase to the plateau phase; from day 6 to day 10, the surviving cell density is substantially steady, with a maximum cell density of $1.2 \times 10^7$/mL and a cell survival rate of 90% or higher. In the course of cultivation, rhNGF concentration increases rapidly and continuously so as to reach 78 mg/L at the end of cultivation.

Embodiment 4: Biological Activity of rhNGF is Assessed by TF-1 Cell/MTS Colorimetry TF-1 cell/MTS colorimetry is a classic method described in Volume III, the Pharmacopoeia of the People's Republic of China, published in year 2015, and adapted to measure biological activity of neural growth factors. The biological activity of rhNGF is measured by this method and compared with an international standard product (lot number: 93/556, NIBSC), mNGF (Sutaisheng, Mouse Nerve Growth Factor for Injection, Staidson (Beijing) Biont Pharmaceuticals Co., Ltd.)

Figure 8:
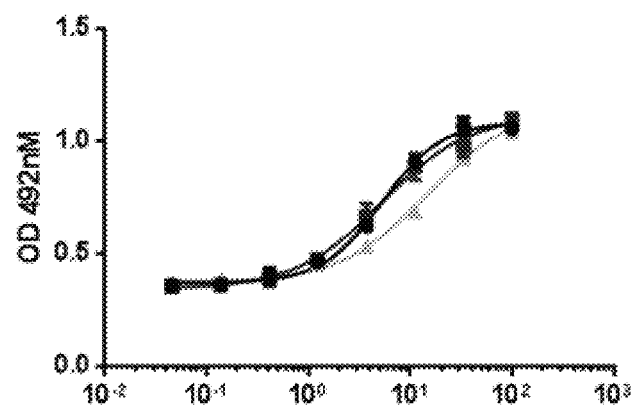
FIG. 8: Curve of activity of TF-1 cell reproduction stimulated by rhNGF and measured by TF-1 cell/MTS colorimetry

Basic culture medium (1640+10% FBS+1% P/S) for well-grown human erythrocyte leukemia cells (TF-1 cells, acclimated NGF-dependent, source: Recombinant Albumen Office, National Institutes for Food and Drug Control) is introduced into a 96-well plate, 5000 cells per well, 100 μL per well. Then, 100 μL of NGF (rhNGF, an international standard product (Std), Sutaisheng) solution which is 3-fold serially diluted with basic culture medium is added to each well, with concentrations of 100, 33, 11, 3.3, 1.1, 0.33, 0.11, 0.033 ng/mL, and each concentration is allocated to two wells in duplicate. After being blended, the NGF solution is cultured for 72 hours in a 5% $CO_2$ incubator at 37° C. After that, 20 μL of MTS is added to each well at 37° C., blended and incubated for three hours. The OD value of each well is detected with an enzyme-labeled instrument at 492 nm. Each absorbance—concentration relation curve is constructed by performing curve fitting (using non-linear regression equations of four parameters) with Graphpad 6.0 software. The $EC_{50}$ value of TF-1 cells reproduced under the stimulation by each sample is calculated, and the result is shown in FIG. 8.

The result is as follows: rhNGF equals the international standard product (Std) ($EC_{50}$ of 5.30 ng/mL, 5.26 ng/mL) and surpasses Sutaisheng ($EC_{50}$ of 14.82 ng/mL) in stimulating TF-1 cell reproduction activity.

| Sequence Listing Information |
|---|
| SEQ ID NO. 1: nucleotide sequence of "gene C" glo |
| CTCGACTGATCACAGGTAAGTATCAAGGTTACAAGACAGGTTTAAGGAGA |
| CCAATAGAAACTGGGCTTGTCGAGACAGAGAAGACTCTTGCGTTTCTGAT |
| AGGCACCTATTGGTCTTACTGACATCCACTTTGCCTTTCTCTCCACAGGT |
| SEQ ID NO. 2: nucleotide sequence of "gene C" aden |
| GAATTAATTCGCTGTCTGCGAGGGCCAGCTGTTGGGGTGAGTACTCCCTC |
| TCAAAAGCGGGCATGACTTCTGCGCTAAGATTGTCAGTTTCCAAAAACGA |

| Sequence Listing Information |
|---|
| GGAGGATTTGATATTCACCTGGCCCGCGGTGATGCCTTTGAGGGTGGCCG |
| CGTCCATCTGGTCAGAAAAGACAATCTTTTTGTTGTCAAGCTTGAGGTGT |
| GGCAGGCTTGAGATCTGGCCATACACTTGAGTGACAATGACATCCACTTT |
| GCCTTTCTCTCCACAGGTGTCCACTCCCAGGTCCAACTGCAGGTCG |
| SEQ ID NO. 3: nucleotide sequence of "gene B" Pre |
| ATGGACTCTAAAGGCTCCTCTCAGAAGGGTAGTAGGCTGCTGCTGCTGCT |
| GGTGGTGTCAAATCTGCTGCTGTGCCAGGGGGTCGTCAGC |
| SEQ ID NO. 4: amino acid sequence of "gene B" Pre |
| MDSKGSSQKGSRLLLLLVVSNLLLCQGVVS |
| SEQ ID NO. 5: nucleotide sequence of "gene B" Luc |
| ATGGGTGTCAAGGTCCTGTTCGCACTGATTTGTATCGCCGTCGCAGAAGC |
| C |
| SEQ ID NO. 6: amino acid sequence of "gene B" Luc |
| MGVKVLFALICIAVAEA |
| SEQ ID NO. 7: nucleotide sequence of proNGF |
| GAGCCTCATAGTGAATCAAACGTGCCTGCTGGCCACACCATCCCACAGGC |
| ACATTGGACAAAGCTGCAGCACAGCCTGGACACAGCTCTGAGGCGGGCAC |
| GCTCTGCCCCAGCCGCTGCAATCGCCGCTCGCGTCGCCGGACAGACTCGA |
| AATATTACCGTGGACCCCAGGCTGTTCAAGAAAAGACGCCTGCGATCACC |
| TCGTGTCCTGTTTTCCACTCAGCCCCCTCGAGAGGCAGCCGATACCCAGG |
| ACCTGGATTTCGAAGTGGGCGGAGCTGCACCCTTCAACAGGACCCACCGG |
| AGTAAGAGATCCAGCTCTCACCCCATCTTCCATCGGGGGAGTTCTCCGT |
| GTGCGATTCCGTGAGCGTCTGGGTGGGTGACAAAACCACAGCTACAGATA |
| TCAAGGGCAAAGAGGTCATGGTGCTGGGAGAAGTCAATATTAACAATTCC |
| GTGTTCAAGCAGTACTTCTTTGAAACTAAATGCCGTGACCCAAACCCCGT |
| CGATTCCGGGTGTAGAGGTATTGACTCTAAGCATTGGAATAGTTATTGTA |
| CTACCACACACACATTTGTGAAGGCCCTGACTATGGATGGCAAACAGGCC |
| GCTTGGAGATTCATTCGTATTGACACTGCTTGCGTCTGCGTGCTGAGTCG |
| TAAGGCTGTGCGG |
| SEQ ID NO. 8: amino acid sequence of proNGF |
| EPHSESNVPAGHTIPQAHWTKLQHSLDTALRRARSAPAAAIAARVAGQTR |
| NITVDPRLFKKRRLRSPRVLFSTQPPREAADTQDLDFEVGGAAPFNRTHR |
| SKRSSSHPIFHRGEFSVCDSVSVWVGDKTTATDIKGKEVMVLGEVNINNS |
| VFKQYFFETKCRDPNPVDSGCRGIDSKHWNSYCTTTHTFVKALTMDGKQA |
| AWRFIRIDTACVCVLSRKAVR |
| SEQ ID NO. 9: nucleotide sequence of "gene B" Nat |
| ATGTCAATGCTGTTTTACACTCTGATTACCGCTTTTCTGATCGGAATCCA |
| GGCC |
| SEQ ID NO. 10: amino acid sequence of "gene B" Nat |
| MSMLFYTLITAFLIGIQA |

What is claimed is:

1. A human nerve growth factor pro gene nucleic acid molecule, comprising the nucleotide sequence SEQ ID NO: 7.

2. A nucleic acid molecule for expression of rhNGF, wherein the nucleic acid molecule comprises the nucleotide sequence SEQ ID NO: 7, operably linked to the nucleotide sequence of SEQ ID NO: 3 or SEQ ID NO: 5.

3. A method of producing rhNGF, comprising:
producing rhNGF by expression of the nucleic acid molecule of claim 2.

4. The nucleic acid molecule of claim 2, further comprising the nucleotide sequence of SEQ ID NO: 1 or SEQ ID NO: 2 operably linked to the nucleotide sequence of SEQ ID NO: 3 or SEQ ID NO: 5.

5. A method of producing rhNGF, comprising:
producing rhNGF by expression of the nucleic acid molecule of claim 4.

6. A method of producing rhNGF, comprising:
producing rhNGF by expression of a nucleic acid molecule comprising a nucleotide sequence SEQ ID NO: 3 or SEQ ID NO: 5.

* * * * *